United States Patent [19]

Hefner, Jr.

[11] Patent Number: 4,612,359

[45] Date of Patent: Sep. 16, 1986

[54] ESTERIFIED POLYCYANATE COMPOSITIONS AND THERMOSET RESINS THEREOF

[75] Inventor: Robert E. Hefner, Jr., Lake Jackson, Tex.

[73] Assignee: The Dow Chemical Company, Midland, Mich.

[21] Appl. No.: 787,938

[22] Filed: Oct. 16, 1985

Related U.S. Application Data

[63] Continuation-in-part of Ser. No. 714,645, Mar. 21, 1985, abandoned.

[51] Int. Cl.$^4$ .............................................. C08G 83/00
[52] U.S. Cl. ........................................ 528/97; 528/99; 528/119; 528/120; 528/363; 528/365; 525/504; 525/481; 560/301; 558/269
[58] Field of Search .................... 528/99, 119, 120, 97, 528/363, 365; 525/504, 481; 260/453 AR, 453 AM

[56] References Cited

U.S. PATENT DOCUMENTS

| | | |
|---|---|---|
| 4,094,852 | 6/1978 | Sundermann et al. |
| 4,142,034 | 2/1979 | Schroll .................. 528/120 |
| 4,373,086 | 2/1983 | Ikeguchi ................ 528/363 |
| 4,393,195 | 7/1983 | Gaku et al. ............ 528/119 |
| 4,477,629 | 10/1984 | Hefner .................. 528/99 |
| 4,489,202 | 12/1984 | Hefner .................. 528/99 |
| 4,533,727 | 8/1985 | Gaku et al. ............ 528/363 |

*Primary Examiner*—John Kight
*Assistant Examiner*—M. L. Moore
*Attorney, Agent, or Firm*—J. G. Carter

[57] ABSTRACT

Thermosettable compositions are prepared which contain (A) from about 0.1 to 100 percent by weight of an esterified aromatic cyanate; (B) from zero to about 99.9 percent by weight of an aromatic polycyanate, an aromatic polycyanamide or mixture thereof and (C) from zero to about 99.9 percent by weight of an epoxy resin.

14 Claims, No Drawings

ESTERIFIED POLYCYANATE COMPOSITIONS AND THERMOSET RESINS THEREOF

CROSS REFERENCE TO RELATED APPLICATION

This application is a continuation-in-part of application Ser. No. 714,645 filed Mar. 21, 1985, now abandoned.

BACKGROUND OF THE INVENTION

This invention pertains to thermosettable resin compositions having improved mechanical properties.

Resins containing the cyanate group or the cyanamide group are known and are thermosettable to polytriazines. Said polytriazines have excellent heat resistance, however, there is substantial room for improvement in their mechanical properties. U.S. Pat. No. 4,094,852 teaches the use of high boiling esters as plasticizers in cyanate resins. Although said esters improve some mechanical properties, they are not chemically bonded to the thermoset resin and may thus be easily leached out of the resin resulting in a decrease in mechanical properties.

The present invention provides novel cyanate resin compositions and novel cyanamide resin compositions which contain chemically bonded ester groups. Said compositions are thermosettable to useful polymeric (cured) compositions with improved mechanical strength. These compositions are useful in the preparation of castings, laminates or composites, coatings, and the like.

SUMMARY OF THE INVENTION

The present invention concerns thermosettable compositions which comprise (A) from about 0.1 to 100, preferably from about 1 to about 50, most preferably from about 5 to about 25, percent by weight (pbw) of at least one esterified aromatic cyanate represented by the formulas

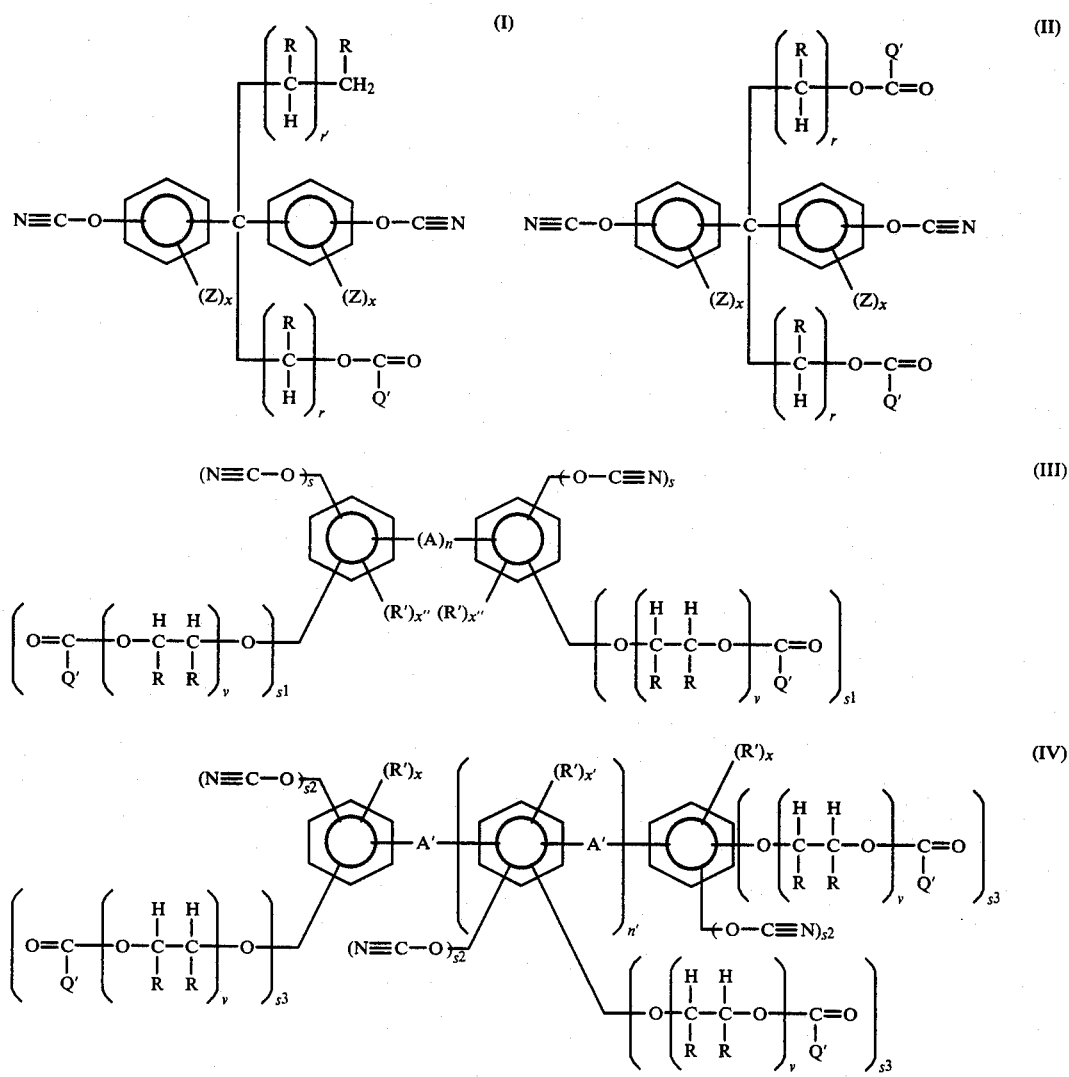

-continued

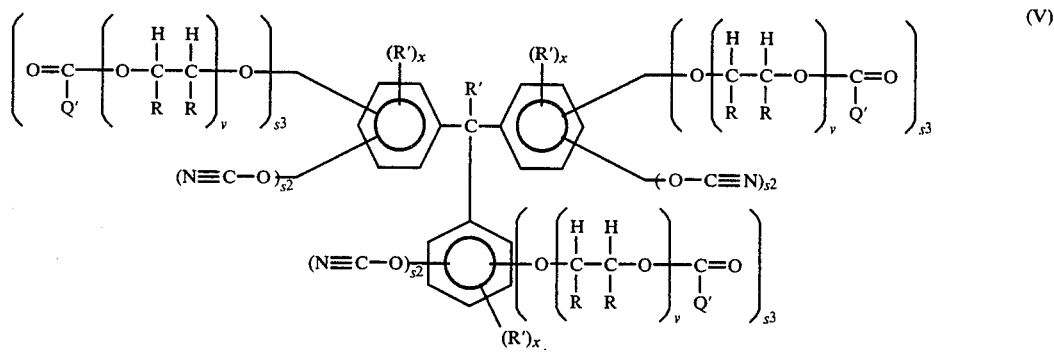

wherein each Q' is a saturated or unsaturated hydrocarbyl group containing from about 2 to about 36 carbon atoms; each A is independently a divalent hydrocarbon group having from 1 to about 10 carbon atoms, preferably from 1 to about 4 carbon atoms, —O—,

—S—, —S—S—,

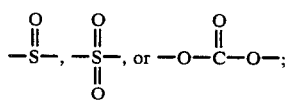

each A' is independently a divalent hydrocarbon group having from 0.001 to about 6, preferably from 0.01 to about 4 carbon atoms or a

group; p has a value of from zero to about 10, preferably from zero to 3; each R' is independently hydrogen, a hydrocarbyl or hydrocarbyloxy group having from 1 to about 10, preferably 1 to about 4 carbon atoms or halogen, preferably chlorine or bromine; each Z is independently hydrogen, a hydrocarbyl or hydrocarbyloxy group having from 1 to about 10, preferably 1 to about 4 carbon atoms, chlorine, bromine, a phenyl group or a —O—C≡N group; each R is independently hydrogen or a methyl group; n has a value of zero or 1; n' has a value from 0.001 to about 6, preferably from about 0.01 to about 3; x has a value of 4; x' has a value of 3; x" has a value of 4 when $s+s^1$ has a value of 1 per each aromatic ring; x" has a value of 3 when $s+s^1$ has a value of 2 per each aromatic ring; r has a value from 1 to about 36; r' has a value from zero to about 36; v has a value from 1 to about 10, preferably 1 to about 3; s has a value from about 0.1 to about 0.99 when $s+s^1$ has a value of 1 per each aromatic ring; $s^1$ has a value from zero to about 0.9 when $s+s^1$ has a value of 1 per each aromatic ring with the proviso that $s^1$ on at least one ring is not zero; s has a value from about 0.1 to about 1.99 when $s+s^1$ has a value of 2 per each aromatic ring; $s^1$ has a value from about zero to about 1.9 when $s+s^1$ has a value of 2 per each aromatic ring with the proviso that $s^1$ on at least one ring is not zero; $s^2$ has a value from about 0.1 to about 0.99 when $s^2+s^3$ has a value of 1 per each aromatic ring and $s^3$ has a value from about zero to about 0.9 when $s^2+s^3$ has a value of 1 per each aromatic ring with the proviso that $s^3$ on at least one ring is not zero;

(B) from zero to about 99.9, preferably from about 10 to about 75, most preferably from about 25 to about 50, pbw of
   (1) aromatic polycyanate,
   (2) an aromatic polycyanamide or
   (3) any combination thereof represented by the formulas

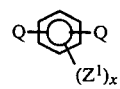

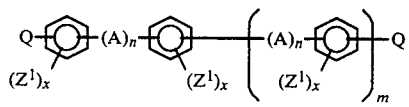

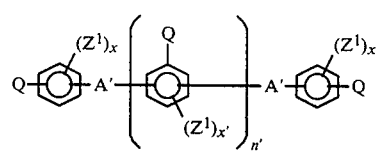

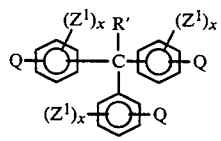

wherein each A, A', R', x, x', n and n' are as hereinbefore defined; each Q is independently a —O—C≡N or

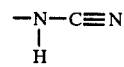

group; each $Z^1$ is independently hydrogen, a hydrocarbyl or hydrocarbyloxy group having from 1 to about 10, preferably 1 to about 4 carbon atoms, chlorine, bromine, a —O—C≡N group or a

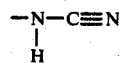

group and m has a value from zero to about 100, preferably from zero to about 10; and (C) from zero to about 99.9, preferably from 10 to about 75, most preferably from 25 to about 60, pbw of an epoxy resin having an average of more than one vicinal epoxide group per molecule or mixture of such epoxy resins represented by the formulas

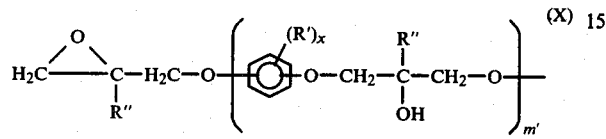

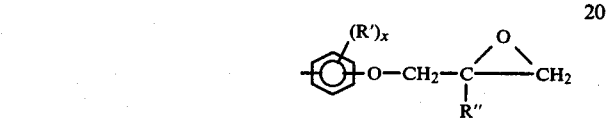

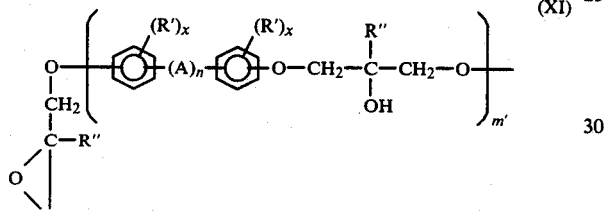

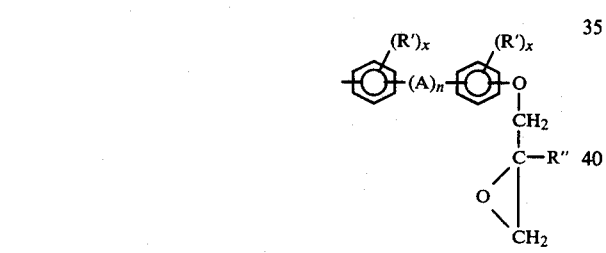

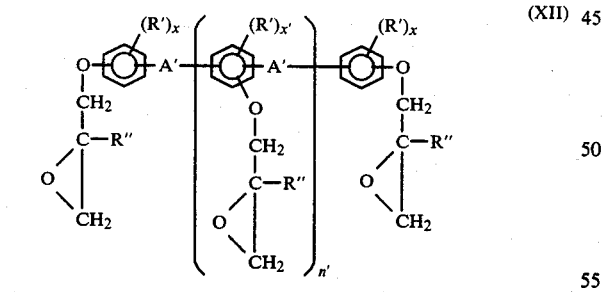

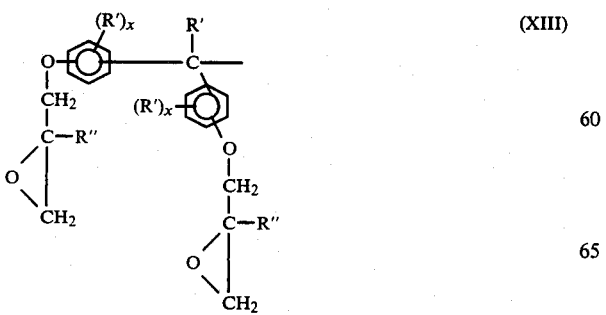

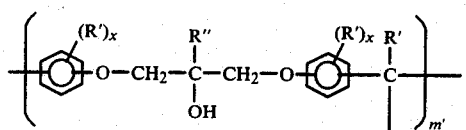

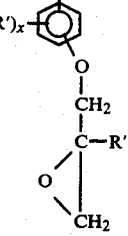

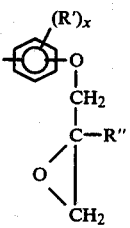

wherein each A, A', R', x, x', n and n' are as hereinbefore defined; each R'' is independently hydrogen or a hydrocarbyl group having from 1 to about 3 carbon atoms and m' has a value from zero to about 40, preferably from 0.1 to about 5.

The above references to percent by weight (pbw) pertain to the combined weight of components (A), (B) and (C).

DETAILED DESCRIPTION OF THE INVENTION

The esterified aromatic cyanates employed herein which are represented by formulas I and II are prepared by reaction of a stoichiometric or a slight stoichiometric excess (up to about 20 percent excess) of a cyanogen halide and a stoichiometric quantity of a base per hydroxyl group with an aromatic polyphenol containing pendant carboxylic acid ester functionality represented by the formulas

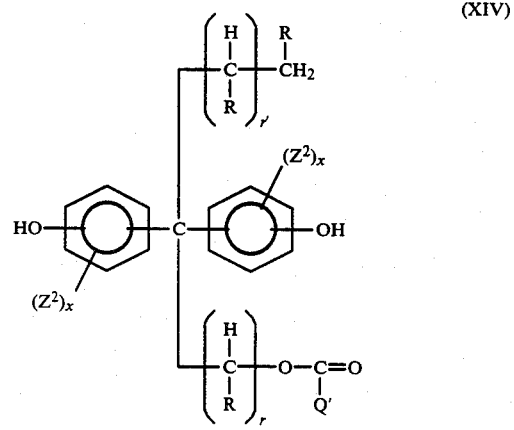

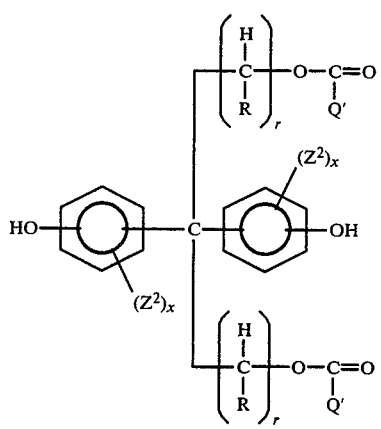

(XV)

respectively, wherein Q', R, r, r' and x are as hereinbefore defined and each $Z^2$ is independently hydrogen, a hydrocarbyl or hydrocarbyloxy group having from 1 to about 10, preferably 1 to about 4 carbon atoms, chlorine, bromine or a hydroxyl group. Suitable cyanogen halides include cyanogen bromide and cyanogen chloride. Alternately, the method of Martin and Bauer described in *Organic Synthesis*, Volume 61, pp. 35–68 (1983) and published by John Wiley and Sons can be used to generate the required cyanogen halide in situ from sodium cyanide and a halogen such as chlorine or bromine. Suitable bases include both inorganic bases and tertiary amines such as sodium hydroxide, potassium hydroxide, triethylamine, mixtures thereof and the like. Most preferred as the base is triethylamine. Suitable solvents include water, acetone, chlorinated hydrocarbons, ketones, and the like. Most preferred solvents are acetone and methylene chloride. Reaction temperatures of from about −40° to about 60° C. are operable with temperatures of −20° to 25° C. being preferred.

The term hydrocarbyl as employed herein means any aliphatic, cycloaliphatic, aromatic aryl substituted aliphatic or aliphatic substituted aromatic groups. Likewise, the term hydrocarbyloxy group means hydrocarbyl group having an oxygen linkage between it and the object to which it is attached.

Particularly suitable esterified aromatic cyanates represented by formulas I or II which can be employed herein include, for example,

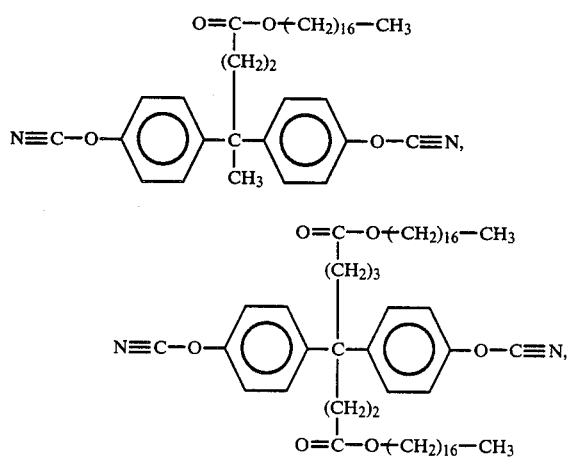

mixtures thereof and the like.

The esterified aromatic cyanates employed herein which are represented by formulas II, IV and V are prepared by reaction of an alkylene oxide with a portion of the hydroxyl groups of an aromatic polyphenol followed by esterification of the hydroxyalkyl groups of the resultant partially hydroxyalkylated polyphenol using a stoichiometric quantity (based on hydroxyalkyl groups) of a saturated and/or unsaturated aliphatic monocarboxylic acid then reaction of a stoichiometric or a slight stoichiometric excess (up to about 20 percent excess) of a cyanogen halide and a stoichiometric quantity of a base per hydroxyl group remaining in the aromatic polyphenol.

Suitable polyphenols include those represented by formulas

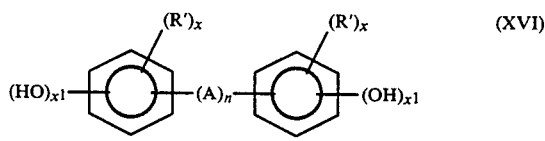

(XVI)

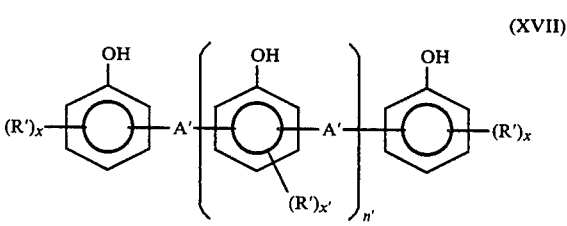

(XVII)

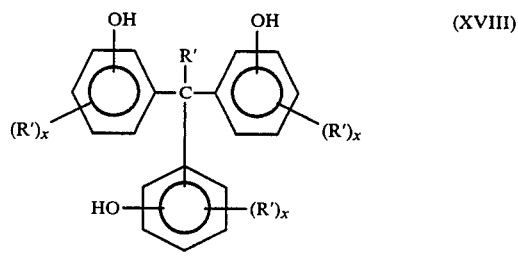

(XVIII)

respectively, wherein R', A, A', x, x', n and n' are as hereinbefore defined and each $x^1$ has a value of 1 or 2.

Suitable alkylene oxide include ethylene oxide, propylene oxide, butylene oxide, isobutylene oxide, amylene oxide, cyclohexene oxide, mixtures thereof and the like. In the reaction of an alkylene oxide with a portion of the hydroxyl groups of an aromatic polyphenol, at least 0.01 but no more than 0.9, preferably 0.01 to about 0.3, most preferably 0.03 to about 0.15 mole percent of the total phenolic hydroxyl groups are reacted. A catalyst is optionally, although preferably used in said reaction. Suitable catalysts include both acidic and basic catalysts. A most preferred catalyst is boron trifluoride etherate. Reaction temperatures of from about 25° to about 125° C. are operable with temperature of from about 30° to about 70° C. being preferred. A solvent is optionally used in said reaction and is selected from those which are inert to the reaction. Suitable solvents include aliphatic ethers, cyclic ethers, chlorinated hydrocarbons, and the like. A most preferred solvent is p-dioxane. Suitable saturated and/or unsaturated aliphatic monocarboxylic acids include those containing from about 2 to about 36 carbon atoms. Typical of said acids are hexanoic acid, hexenoic acid, octanoic acid, dodecanoic acid, oleic acid, stearic acid, mixtures thereof and the like. Saturated aliphatic monocarboxylic acids are most preferred. Reaction temperatures of from about 125° to about 250° C. are operable with temperatures of from about 175° to 225° C. being preferred. A solvent is optionally used in said reaction to assist in removal of water from the esterification reaction by formation of an azeotrope. Preferred solvents include toluene, xylene and the like. Cyanation reaction of the esterified partially hydroxyalkylated polyphenol is completed using the previously described method.

The esterified aromatic cyanates which are represented by formulas III, IV and V may be pure compounds or preferably, mixtures. A particularly suitable esterified aromatic cyanate represented by formula III is the partial cyanate of the stearic acid ester of partially propoxylated bisphenol A wherein the total of both s groups is 0.9 mole percent and the total of both $s^1$ groups is 0.1 mole percent and $s+s^1$ has a value of 1 per each aromatic ring. Mixtures containing said esterified aromatic cyanates represented by formulas III, IV and V may contain up to about 98 percent by weight (pbw) of an aromatic polycyanate represented by formulas VII, VIII, and IX where Q is a —O—C≡N group, respectively and up to about 40 pbw of the saturated and/or unsaturated aliphatic monocarboxylic acid ester of a totally hydroxyalkylated polyphenol represented by formula III where $s=0$ and $s^1=1$ or 2, formula IV where $s^2=0$ and $s^3=1$, and formula V where $s^2=0$ and $s^3-1$, respectively. Particularly suitable esterified aromatic cyanate mixtures represented by formulas III, IV and V include those wherein the saturated and/or unsaturated aliphatic monocarboxylic acid ester of a totally hydroxyalkylated polyphenol ($s=0$ and $s^1=1$ or 2 or $s^2=0$ and $s^3-1$) is present at less than about 1 pbw.

The aromatic polycyanates optionally employed herein which are represented by formulas VI, VII, VIII and IX where Q is a —O—C≡N group are prepared by reaction of a stoichiometric or slight stoichiometric excess (up to about 20 percent excess) of a cyanogen halide and a stoichiometric quantity of a base per hydroxyl group with an aromatic polyphenol represented by the aforementioned formulas XVII or XVIII and by the formulas

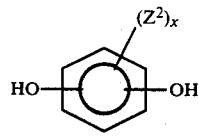
(XIX)

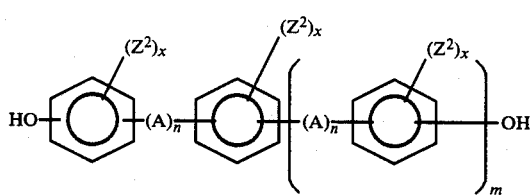
(XX)

where A, A', R', $Z^2$, x, x', n, n' and m are as hereinbefore defined. Cyanation reaction is completed using the previously described method.

Particularly suitable aromatic polycyanates which can be employed herein include, for example, bisphenol A dicyanate, the dicyanates of 4,4'-dihydroxydiphenyl oxide, resorcinol, 4,4'-thiodiphenol, 4,4'-sulfonyldiphenol, 3,3',5,5'-tetrabromobisphenol A, 2,2',6,6'-tetrabromobisphenol A, 3-phenylbisphenol A, 4,4'-dihydroxybiphenyl, 2,2'-dihydroxybiphenyl, 2,2',4,4'-tetrahydroxydiphenyl methane, 2,2',6,6'-tetramethyl-3,3',5,5'-tetrabromobisphenol A, 3,3'-dimethoxybisphenol A, the bisphenol of dicyclopentadiene, the bisphenol of tricyclopentadiene,

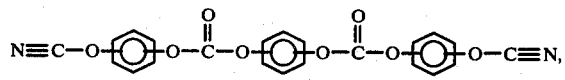

the polycyanate of a phenolformaldehyde condensation product (novolac), the polycyanate of a phenol-dicyclopentadiene condensation product and the polycyanate of 2,2',4,4'-tetrahydroxydiphenyl methane, mixtures thereof and the like.

The aromatic polycyanamides optionally employed herein which are represented by formulas VI, VII, VIII and IX where Q is a

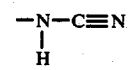

group are prepared by reaction of a stoichiometric or slight stoichiometric excess (up to about 20 percent excess) of a cyanogen halide and a stoichiometric quantity of a base per hydroxyl group with an aromatic polyamine represented by the formulas

(XXI)

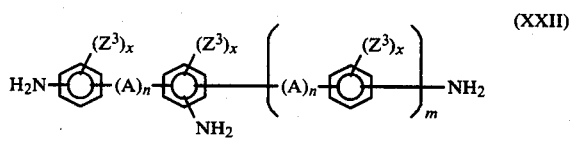
(XXII)

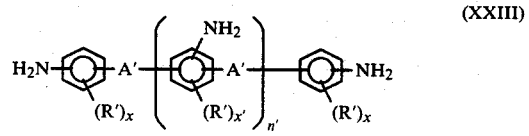
(XXIII)

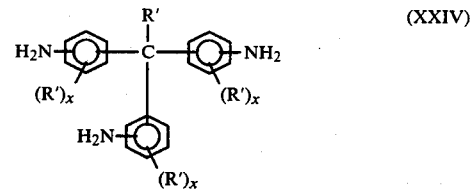
(XXIV)

where A, A', R', x, x', n, n' and m are as hereinbefore defined and each $Z^3$ is independently hydrogen, a hydrocarbyl or hydrocarbyloxy group having from 1 to about 10, preferably 1 to about 4 carbon atoms, chlorine, bromine or a —NH₂ group. The aforementioned methods used to prepare the aromatic polycyanates are generally useful for the preparation of aromatic polycyanamides.

Particularly suitable aromatic polycyanamides which can be employed herein include, for example, the dicyanamides of 4,4'-isopropylidenedianiline, 4,4'-diaminodiphenyl oxide, 1,3-diaminobenzene, 4,4'-diaminodiphenyl sulfide, 4,4'-diaminodiphenyl sulfone, 2,2',6,6'-tetrabromo-4,4'-isopropylidenedianiline, 3-phenyl-4,4'-isopropylidenedianiline, 4,4'-diaminodiphenyl, 2,2'-diaminodiphenyl, 2,2',4,4'-tetraaminodiphenyl methane, 2,2',6,6'-tetramethyl-3,3',5,5'-tetrabromo-4,4'-isopropylidenedianiline, 3,3'-dimethoxy-4,4'-isopropylidenedianiline, the dianiline of dicyclopentadiene, the dianiline of tricyclopentadiene,

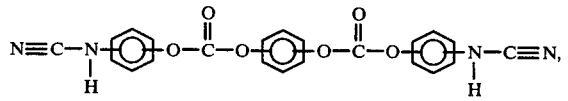

the polycyanamide of an aniline-formaldehyde condensation product, the polycyanamide of an aniline-dicyclopentadiene condensation product and the polycyanamide of 2,2',4,4'-tetraaminodiphenyl methane, mixtures thereof and the like.

The polyepoxides optionally employed herein which are represented by formulas X, XI, XII and XIII are prepared by reaction of a diphenol or polyphenol represented by the aforementioned formulas XVII or XVIII and formulas XXV or XXVI wherein A, R', x and n are as hereinbefore defined with an epihalohydrin and a basic-acting material. Said reaction generally involves two distinct steps: coupling reaction of the epihalohydrin and diphenol or polyphenol to provide a halohydrin intermediate and dehydrohalogenation reaction of the halohydrin intermediate to provide the glycidyl ether product. Suitable catalysts and reaction conditions for preparing polyepoxides are described in the *Handbook of Epoxy Resins* by Lee and Neville, McGraw-Hill (1967) which is incorporated herein be reference.

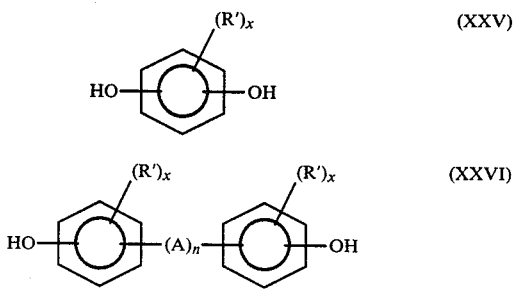

Particularly suitable polyepoxides which can be employed herein include, for example, the diglycidyl ethers of resorcinol, bisphenol A, 3,3',5,5'-tetrabromobisphenol A, the triglycidyl ether of tris(hydroxyphenyl)methane, the polyglycidyl ether of a phenol-formaldehyde condensation product (novolac), the polyglycidyl ether of a dicyclopentadiene and phenol condensation product and the like. The polyepoxides can be used either alone or in combination.

Compositions which comprise an esterified aromatic cyanate (formulas I, II, III, IV, V) or mixtures thereof may be cured (polymerized) by heating from 50° C. to 350° C. or more, preferably by heating from 70° C. to 200° C. and optionally in the presence of 0.001 to 5 percent of a suitable trimerization catalyst. Operable trimerization catalysts include those taught by Oehmke in U.S. Pat. No. 3,694,410 and Sundermann, et al in U.S. Pat. No. 4,094,852. Most preferred trimerization catalysts are cobalt naphthenate and cobalt octoate. Prepolymerization (B-staging) may be effected by using lower cure temperatures and/or shorter curing times. Curing of the prepolymerized resin may then be completed at a later time or immediately following prepolymerization to comprise a single curing step.

The cured products are polytriazines wherein the ester groups are chemically bonded to the polymer chains. It is to be understood that the term polytriazine can also include lesser amounts of other curing structures.

Compositions which comprise an esterified aromatic cyanate (formulas I, II, III, IV, V) or mixtures thereof and an aromatic polycyanate, polycyanamide (formulas VI, VII, VIII, IX where Q is a —O—C≡N group or a

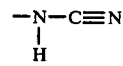

group, respectively) or mixtures thereof may be cured (copolymerized) as previously described. The cured products are polytriazines wherein the ester groups are chemically bonded to the polymer chains.

Compositions which comprise an esterified aromatic cyanate (formulas I, II, III, IV, V) or mixtures thereof and a polyepoxide (formulas X, XI, XII, XIII) or mixtures thereof may be cured (copolymerized) using the methods previously described for curing of the esterified aromatic cyanates.

Compositions which comprise an esterified aromatic cyanate (formulas I, II, III, IV, V) or mixtures thereof, a polyepoxide (formulas X, XI, XII, XIII) or mixtures thereof, and an aromatic polycyanate, polycyanamide (formulas VI, VII, VIII, IX where Q is a —O—C≡N group or a

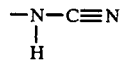

group, respectively) or mixtures thereof may be cured (copolymerized) using the methods previously described for curing of the esterified aromatic cyanates.

The compositions of the present invention are useful in the preparation of castings, laminates or composites, coatings and the like, especially where high mechanical strength or toughness is desired.

In the preparation of laminates or composites from the compositions of the present invention, suitable substrates include, but are not limited to, woven and non-woven fibers and/or filaments of glass, carbon, graphite, boron, aramid, asbestos, glass and carbon hybrids, combinations thereof and the like.

The following examples are illustrative of the invention, but are not to be construed as to limiting the scope thereof in any manner.

EXAMPLE 1

A. Preparation of Dicyanate of Diphenolic Acid Stearyl Ester

A 53.88 gram (0.10 mole) portion of the stearyl ester of diphenolic acid

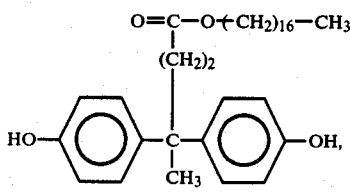

22.25 grams (0.21 mole) of cyanogen bromide and 300 milliliters of acetone were added to a reactor and maintained under a nitrogen atmosphere with stirring. The stirred solution was chilled to −5° C. then 20.34 grams (0.201 mole) of triethylamine was added to the reactor over a fifteen minute (900 s) period and so as to maintain the reaction temperature at −5° to −1° C. After completion of the triethylamine addition, the reactor was maintained at −5° to −4° C. for an additional fifty-five minutes (3300 s), followed by addition of the reactor contents to 1 gallon (3.79 l) of deionized water. After five minutes (300 s), the water and product mixture was mutliply extracted with three 250 milliliter volumes of methylene chloride. The combined methylene chloride extract was washed with 200 milliliters of one percent aqueous hydrochloric acid followed by washing with 500 milliliters of deionized water then drying over anhydrous sodium sulfate. The dry methylene chloride extract was filtered and solvent removed by rotary evaporation under vacuum. The dicyanate of diphenolic acid stearyl ester (53.9 grams) was recovered in 91.5 percent yield as a white colored wax. Infrared spectrophotometric analysis of a film sample of the product confirmed the product structure (disappearance of phenolic hydroxyl group, appearance of —O—C≡N group, presence of ester group).

B. Preparation of Bisphenol A Dicyanate

A 456.60 gram (2.00 mole) portion of 4,4'-isopropylidenediphenol, 444.91 grams (4.20 moles) of cyanogen bromide and 1000 milliliters of acetone were added to a reactor and maintained under a nitrogen atmosphere with stirring. The stirred solution was cooled to −5° C. then 406.82 grams (4.02 moles) of triethylamine was added to the reactor over a thirty minute (1800 s) period and so as to maintain the reaction temperature at −5° to −2° C. After completion of the triethylamine addition, the reactor was maintained at −5° to −3° C. for an additional forty-five minutes (2700 s), followed by addition of the reactor contents of 1.5 gallons (5.69 l) of deionized water. After 5 minutes (300 s) the water and product mixture was extracted with three 500 milliliter volumes of methylene chloride. The combined methylene chloride extract was washed with 500 milliliters of one percent aqueous hydrochloric acid followed by washing with 1000 milliliters of deionized water then drying over anhydrous sodium sulfate. The dry methylene chloride extract was filtered and solvent removed by rotary evaporation under vacuum. Bisphenol A dicyanate (521.2 grams) was recovered in 93.6 percent yield as a white crystalline solid. Infrared spectrophotometric analysis of a film sample of the product confirmed the product structure (disappearance of phenolic hydroxyl group, appearance of —O—C≡N group).

C. Copolymerization of the Dicyanate of Diphenolic Acid Stearyl Ester and Bisphenol A Dicyanate A 25.0 gram (10.0 percent by weight, pbw) portion of the dicyanate of diphenolic acid stearyl ester prepared in A above and a 225.0 gram (90.0 pbw) portion of bisphenol A dicyanate prepared in B above were combined and heated to 50° C. and 0.25 gram of cobalt naphthenate (6.0 percent) was added. This solution was poured into a ⅛ inch (3.175 mm) mold made from a pair of glass plates and then placed in an oven and maintained at 125° C. for 2 hours (7200 s) then 177° C. for 2 hours (7200 s). The transparent, light yellow colored, unfilled casting was demolded and used to prepare test pieces for tensile and flexural strength, flexural modulus, percent elongation and average Barcol hardness (934-1 scale) determinations. Mechanical properties of tensile (6) and flexural (5) test pieces were determined using an Instron machine with standard test methods (ASTM D-638 and D-790). The heat distortion temperature (264 psi) of two test pieces was determined using standard test methods (ASTM D-648 modified). The results are reported in Table I.

COMPARATIVE EXPERIMENT A

Polymerization of Bisphenol A Dicyanate

A 161.3 gram portion of bisphenol A dicyanate prepared using the method of Example 1-B was heated to 60° C. and 0.16 gram of cobalt naphthenate (6.0 percent) was added. This solution was used to prepare a clear, unfilled ⅛ inch (3.175 mm) casting using the method of Example 1-C. The physical and mechanical properties were evaluated using the method of Example 1-C. The results are reported in Table I.

TABLE I

|  | EXAMPLE 1-C | COMPARATIVE EXPERIMENT A |
|---|---|---|
| Barcol Hardness | 46 | 48 |
| Tensile Strength, | | |
| psi | 13,277 | 7,258 |
| kPa | 91,542 | 50,042 |
| Elongation (%) | 2.77 | 1.42 |
| Flexural Strength, | | |
| psi | 23,426 | 11,727 |
| kPa | 161,518 | 80,855 |
| Flexural Modulus, | | |
| psi | 518,000 | 660,000 |
| kPa | 3,571,506 | 4,550,568 |
| Heat Distortion Temperature, °F./°C. | 253.4/123 | NA |

EXAMPLE 2

A. Preparation of a Partial Propoxylate of Bisphenol A

A 228.3 gram (1.00 mole) portion of bisphenol A (4,4'-isopropylidenediphenol), 0.23 gram of boron trifluoride etherate and 300 milliliters of 1,4-dioxane solvent were added to a reactor and maintained under a nitrogen atmosphere with stirring. The stirred solution was heated to 50° C. then 75 grams of propylene oxide were added to the reactor over a twenty minute (1200 s) period and so as to maintain the reaction temperature between 55° and 60° C. During the reaction, excess propylene oxide vented through a chilled water condensor. After completion of the propylene oxide addition, the reactor was maintained at 60° C. for an additional seventy-five minutes (4500 s) followed by rotary evaporation under vacuum to remove solvent and any unreacted propylene oxide. The partial propoxylate of bisphenol A (252.1 grams) was recovered as a tan colored solid. This mass balance of the reaction product demonstrated that addition of 0.4098 mole of propylene oxide to the bisphenol A reactant had occurred. Liquid chromatographic analysis demonstrated that 16 area percent bisphenol A was propoxylated while 84 area percent was unreacted bisphenol A.

B. Esterification of Bisphenol A Partial Propoxylate

The 252.1 grams (0.4098 mole) of the bisphenol A partial propoxylate from A above and 110.81 grams (0.4098 mole) of a monocarboxylic acid mixture composed of 49.89 percent by weight (pbw) stearic acid and 50.11 pbw palmitic acid were added to a reactor and heated to provide a molten solution. Once a solution was obtained, stirring commenced and a nitrogen sparge was maintained at 0.5 LPM with continued heating until a reaction temperature of 225° C. was reached. The 225° C. reaction temperature was maintained for four hours (14,400 s) during which time water from the esterification reaction was sparged from the reactor and into a Dean-Stark trap-cold water condensor assembly. The reactor was cooled to room temperature (25° C.) and the esterified partial propoxylate of bisphenol A (354.9 grams) was recovered as a tan colored wax. Infrared spectrophotometric analysis of a film sample of the product confirmed the product structure (disappearance of carboxylic acid carbonyl group, appearance of carboxylic acid ester carbonyl group).

C. Preparation of Cyanate of Esterified Bisphenol A Partial Propoxylate

A 316.5 gram (1.5902 moles of phenolic hydroxyl groups) portion of the esterified bisphenol A partial propoxylate from C above, cyanogen bromide 176.87 grams (1.67 moles) and 1000 milliliters of acetone were added to a reactor and maintained under a nitrogen atmosphere with stirring. The stirred solution was chilled to −8° C. then 161.73 grams (1.60 moles) of triethylamine was added to the reactor over a thirty minute (1800 s) period and so as to maintain the reaction temperature at −5° to −1° C. After completion of the triethylamine addition, the reactor was maintained at −5° to −1° C. for additional forty-five minutes (2700 s), followed by addition of the reactor contents to 1.5 gallons (5.69 l) of deionized water. After five minutes (300 s) the water and product mixture was multiply extracted with three 500 milliliter volumes of methylene chloride. The combined methylene chloride extract was washed with 500 milliliters of one percent aqueous hydrochloric acid followed by washing with 1000 milliliters of deionized water then drying over anhydrous sodium sulfate. The dry methylene chloride extract was filtered and solvent removed by rotary evaporation under vacuum. The cyanate of esterified bisphenol A partial propoxylate (336.1 grams) was recovered as a light-yellow colored wax. Infrared spectrophotometric analysis of a film sample of the product confirmed the product structure (disappearance of phenolic hydroxyl group, appearance of —O—C≡N group).

D. Copolymerization of the Cyanate of Esterified Bisphenol A Partial Propoxylate and Bisphenol A Dicayante A 66.8 gram (40.0 percent by weight, pbw) portion of the cyanate of esterified bisphenol A partial propoxylate from C above and a 100.2 gram (60 pbw) portion of bisphenol A dicyanate prepared in Example 1-B were combined and heated to 50° C. and 0.17 gram of cobalt naphthenate (6.0 percent active) was added. This solution was used to prepare a clear, unfilled ⅛ inch (3.175 mm) casting using the method of Example 1-C. The transparent, light yellow colored unfilled casting was tested for physical and mechanical properties using the method of Example 1-C. The results are reported in Table II and may be compared with the results of Comparative Experiment A.

TABLE II

| | |
|---|---|
| Barcol Hardness | 43 |
| Tensile Strength, psi/kPa | 9943/68,555 |
| Elongation (%) | 2.03 |
| Flexural Strength, psi/kPa | 17,852/123,086 |
| Flexural Modulus, psi/kPa | 597,000/4,116,196 |
| Heat Distortion Temperature, °F./°C. | 210/99 |

EXAMPLE 3

Copolymerization of the Dicyanate of Diphenolic Acid Stearyl Ester, Bisphenol A Dicyanate and a Diglycidyl Ether of Bisphenol A A 22.0 gram (11.17 pbw) portion of the dicyanate of diphenolic acid stearyl ester prepared in Example 1-A, 70.0 grams (35.56 pbw) of bisphenol A dicyanate prepared in Example 1-B and 104.89 grams (53.27 pbw) of a diglycidyl ether of bisphenol A having an epoxide equivalent weight (EEW) of 181.5 were combined and heated to 50° C. and 0.10 gram of cobalt naphthenate (6.0 percent) was added. This solution was used to prepare a clear, unfilled, ⅛ inch (3.175 mm) casting using the method of Example 1-C. The transparent, light yellow colored unfilled casting was tested for physical and mechanical properties using the method of Example 1-C. The results are reported in Table III.

TABLE III

| | |
|---|---|
| Barcol Hardness | 44 |
| Tensile Strength, psi/kPa | 13,310/91,770 |
| Elongation (%) | 4.49 |
| Flexural Strength, psi/kPa | 24,882/171,556 |
| Flexural Modulus, psi/kPa | 523,000/3,605,980 |
| Heat Distortion Temperature, °F./°C. | 276.4/135.8 |

I claim:

1. A thermosettable composition which comprises
   (A) from about 0.1 to 100 percent by weight (pbw) of the combined weight of components (A), (B) and (C) of at least one esterified aromatic cyanate represented by the formulas I, II, III, IV or V

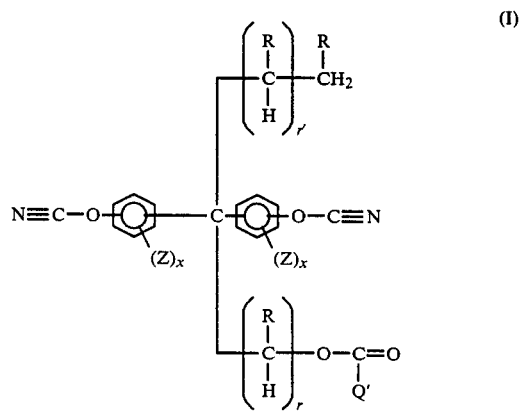

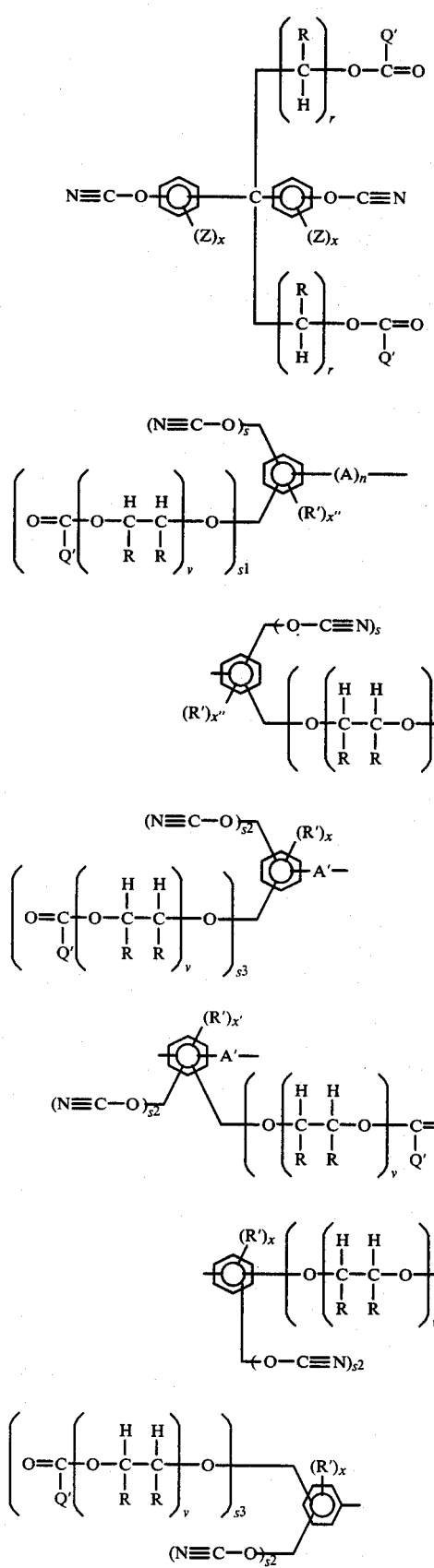

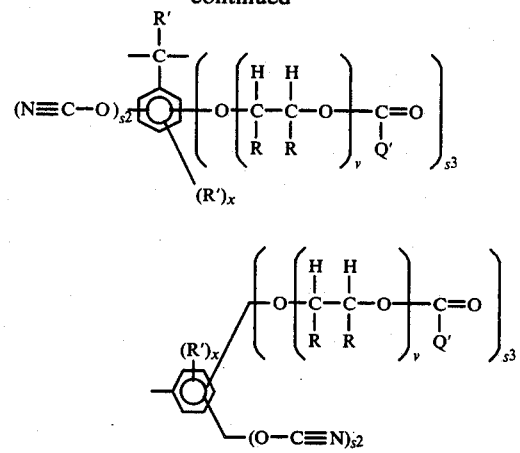

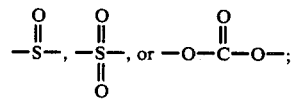

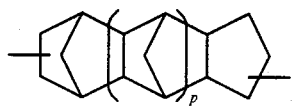

wherein each Q' is a saturated or unsaturated hydrocarbyl group containing from about 2 to about 36 carbon atoms; each A is independently a divalent hydrocarbon group having from 1 to about 10 carbon atoms, —O—,

—S—, —S—S—, $$-\overset{O}{\underset{}{S}}-, \ -\overset{O}{\underset{O}{S}}-, \text{ or } -O-\overset{O}{\underset{}{C}}-O-;$$

each A' is independently a divalent hydrocarbon group having from 0.001 to about 6 carbon atoms or a group; p has a value of from zero to about 10; each R' is independently hydrogen, a hydrocarbyl or hydrocarbyloxy group having from 1 to about 10 carbon atoms or halogen; each Z is independently hydrogen, a hydrocarbyl or hydrocarbyloxy group having from 1 to about 10 carbon atoms, chlorine, bromine or a —O—C≡N group; each R is independently hydrogen or a methyl group; n has a value of zero or 1; n' has a value from 0.001 to about 6; x has a value of 4; x' has a value of 3; x" has a value of 4 when $s+s^1$ has a value of 1 per each aromatic ring; x" has a value of 3 when $s+s^1$ has a value of 2 per each aromatic ring; r has a value from 1 to about 36; r' has a value from zero to about 36; v has a value from 1 to about 10; s has a value from about 0.1 to about 0.99 when $s+s^1$ has a value of 1 per each aromatic ring; $s^1$ has a value from zero to about 0.9 when $s+s^1$ has a value of 1 per each aromatic ring with the proviso that $s^1$ on at least one ring is not zero; s has a value from about 0.1 to about 1.99 when $s+s^1$ has a value of 2 per each aromatic ring; $s^1$ has a value from about zero to about 1.9 when $s+s^1$ has a value of 2 per each aromatic ring with the proviso that $s^1$ on at least one ring is not zero; $s^2$ has a value from about 0.1 to about 0.99 when $s^2+s^3$ has a value of 1 per each aromatic ring and $s^3$ has a value from about zero to about 0.9 when $s^2+s^3$ has a value of 1 per each aromatic ring with the proviso that $s^3$ on at least one ring is not zero;

(B) from zero to about 99.9 pbw of the combined weight of components (A), (B) and (C) of
  (1) an aromatic polycyanate,
  (2) an aromatic polycyanamide or
  (3) any combination thereof represented by the formulas VI, VII, VIII or IX

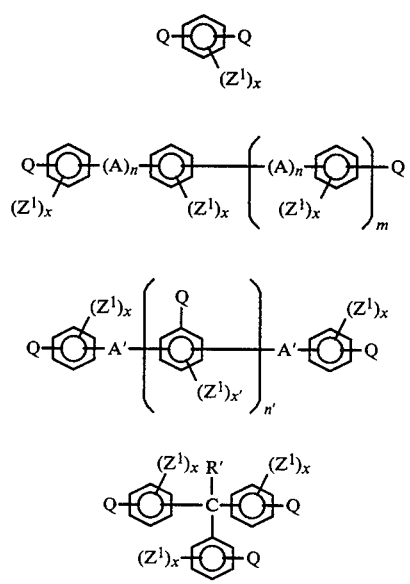

wherein each A, A', R', x, x', n and n' are as above defined; each Q is independently a —O—C≡N or

—N—C≡N
 |
 H group; each $Z^1$ is independently hydrogen, a hydrocarbyl or hydrocarbyloxy group having from 1 to about 10 carbon atoms, chlorine, bromine, a —O—C≡N group or a

—N—C≡N
 |
 H group and m has a value from zero to about 100; and (C) from zero to about 99.9 pbw of the combined weight of components (A), (B) and (C) of an epoxy resin having an average of more than one vicinal epoxide group per molecule or mixture of such epoxy resins represented by the formulas X, XI, XII or XIII

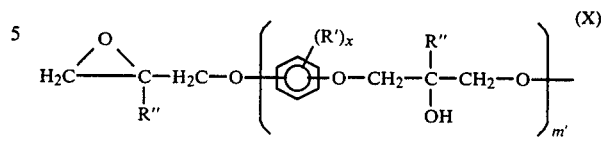

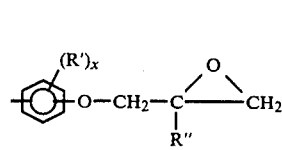

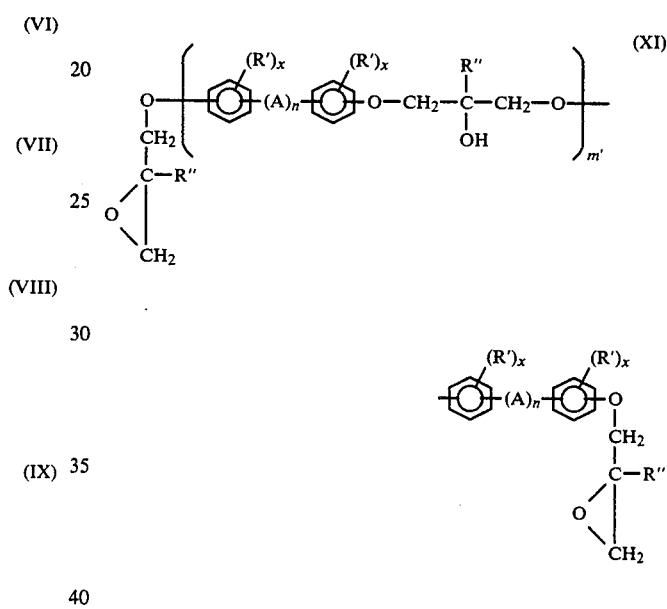

-continued

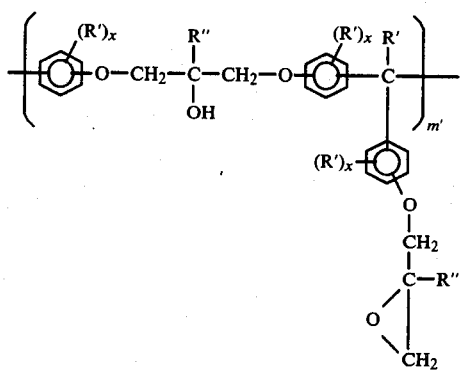

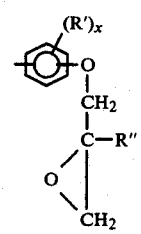

wherein each A, A', R', x, x', n and n' are as above defined; each R" is independently hydrogen or a hydrocarbyl group having from 1 to about 3 carbon atoms and m' has a value from zero to about 40.

2. A thermosettable composition of claim 1 wherein
(i) component (A) comprises from about 1 to about 50 percent by weight;
(ii) component (B) comprises from about 10 to about 75 percent by weight; and
(iii) component (C) comprises from about 10 to about 75 percent by weight.

3. A thermosettable composition of claim 1 wherein
(i) component (A) comprises from about 5 to about 25 percent by weight;
(ii) component (B) comprises from about 25 to about 50 percent by weight; and
(iii) component (C) comprises from about 25 to about 60 percent by weight.

4. A thermosettable composition of claim 1 wherein component (A) is represented by Formula I.

5. A thermosettable composition of claim 4 wherein component (A) is the dicyanate of diphenolic acid stearyl ester.

6. A thermosettable composition of claim 1 wherein component (A) is represented by Formula III.

7. A thermosettable composition of claim 6 wherein component (A) is the cyanate of an esterified bisphenol A partial propoxylate.

8. The product resulting from curing a composition containing a composition of claim 1.

9. The product resulting from curing a composition containing a composition of claim 2.

10. The product resulting from curing a composition containing a composition of claim 3.

11. The product resulting from curing a composition containing a composition of claim 4.

12. The product resulting from curing a composition containing a composition of claim 5.

13. The product resuting from curing a composition containing a composition of claim 6.

14. The product resulting from curing a composition containing a composition of claim 7.

* * * * *